(12) United States Patent
Tichy

(10) Patent No.: US 6,220,386 B1
(45) Date of Patent: Apr. 24, 2001

(54) FLEXIBLE AERODAM TO REDUCE THE SOUND OF TURBULENCE

(76) Inventor: James B. Tichy, P.O. Box 1308, Sausalito, CA (US) 94966

( * ) Notice: Subject to any disclaimer, the term of this patent is extended or adjusted under 35 U.S.C. 154(b) by 0 days.

(21) Appl. No.: 09/411,752

(22) Filed: Oct. 4, 1999

Related U.S. Application Data

(63) Continuation-in-part of application No. 08/896,565, filed on Jul. 18, 1997, now Pat. No. 6,029,769.

(51) Int. Cl.[7] .................................................... H04R 25/00
(52) U.S. Cl. ................................... 181/136; 2/209; 2/423
(58) Field of Search ................................ 181/129, 133, 181/136; 2/209, 423

(56) References Cited

U.S. PATENT DOCUMENTS

| | | | |
|---|---|---|---|
| 4,370,758 | * 2/1983 | Mattheis | ................. 2/423 |
| 5,086,789 | * 2/1992 | Tichy | ..................... 2/209 |
| 5,477,564 | * 12/1995 | Tichy | ..................... 2/209 |
| 6,029,769 | * 2/2000 | Tichy | ................... 181/136 |

* cited by examiner

Primary Examiner—Khanh Dang

(57) ABSTRACT

A boundary layer flow regulator, called a dam, is fastened, by way of example, to a bicycle rider's head band and is located against the temple area. The dam includes a fine permeable maze which viscously impedes but does not arrest the air flow through it. The maze is held in place by a supportive but flexibly resilient, wind permeable matrix attached to a base. On a calm day the relative headwind experienced by the rider is stabilized by the maze held in position by the stilled matrix so that a stationary flow envelope forms around the rider's ear canal to eliminate wind noise. However, on a windy day the preturbulent gusts in the headwind cause the matrix to instantly shift the position and permeability gradient of the maze so that the flow envelope is dynamically regulated around the ear canal to minimize the infranoise caused by the gusts.

20 Claims, 2 Drawing Sheets

FLEXIBLE AERODAM TO REDUCE THE SOUND OF TURBULENCE

CROSS REFERENCE TO RELATED PATENT APPLICATION

This application is a continuation-in-part of application U.S. Ser. No. 08/896,565, filed Jul. 18, 1997 and issued Feb. 29, 2000 as U.S. Pat. No. 6,029,769.

BACKGROUND OF THE INVENTION

Turbulence heard in a headwind flowing by a sound sensitive system, such as the human ear is generated by two sources. The first is locally caused facial turbulence created alongside the human head of, say a bicycle rider because the air flow cannot remain attached past the high curvature of the cheekbone area. Instead, it separates in a turbid flow pattern which results in a noise spectrum varying among individual facial features as well as the relative wind speed, air density and humidity. The second type of turbulence is characteristic of the headwind itself being influenced by atmospheric disturbances: wind, thermals, etc.

Reduction of the first type of flow was addressed in the copending application. The aerodam is designed to attenuate facial turbulence of the bike rider by the use of an open sided filter mounted somewhat perpendicularly to the surface of the human head so that boundary layer stabilization is achieved at two zones: one in front of the aerodam, and the second behind in the wake around the ear canal. The forward zone tends to remain laminar up to the filter because the flow has been pressurized around the convexity of the cheekbone. The rear zone is called the flow envelope because it consists of a laminar wake overflow which encloses a slow flowing null zone caused by a filter. This mimics, in-situ, all those factors that contribute to turbulent decay, namely a diffusion and damping process. The above system assumes a steady headwind, a calm day.

When wearing a fixed aerodam of the type mentioned in U.S. Pat. No. 6,029,769, on a windy day the type-two atmospheric turbulence modulates the forward pressure zone as well as the flow envelope. The results sound like a random low frequency pulsation called infranoise. The atmospheric headwind is comprised of turbulence which can be measured as the time differential of the incoming wind shear per average frontal wind speed, or $d/dt(\text{curl } v/\bar{v})$, or vorticity density. On a calm day the density is zero and the flow envelope pressure over the ear canal is steady. Scaled hydraulic experiments show that the average length and height of the envelope changes little as the flow speed changes. Air cannot flow perpendicularly to the surface so a turbulent vortex flattens out to flow parallel to the surface of the rider's head (Strasberg). This restricts the envelope pressure to vibrate unidirectionally in response to velocity changes in the wind shear patterns which cause changes in the Bernoulli pressure inside the flow envelope over the ear canal. So, not surprisingly, it is the differential change in pressure per increment of time (dp/dt) that is heard.

To protect the flow envelope pressure from vibrating, a commensurate change in the flow gradient of the dam is suggested, such as the height or density of the dam corresponding to the wind shear variation. In nature a narrow vertical tree or shaft of wheat leans over farther as the wind blows harder; the projected height $H_p$ of the shaft decreases and the relation of wind speed v to $H_p$ is negative, or $dH_p/dv<0$. In the fixed aerodam of the prior art the relation is zero or neutral because the matrix is rigid with respect to the wind, or $dH_p/dv=0$. That leaves a third possibility: the higher the instantaneous wind, the higher the structure, $dH_p/dv>0$. This can occur if the structure were flexible and leaned into the wind. It is this structure that shall be studied.

DETAILED DESCRIPTION

Figure 1:
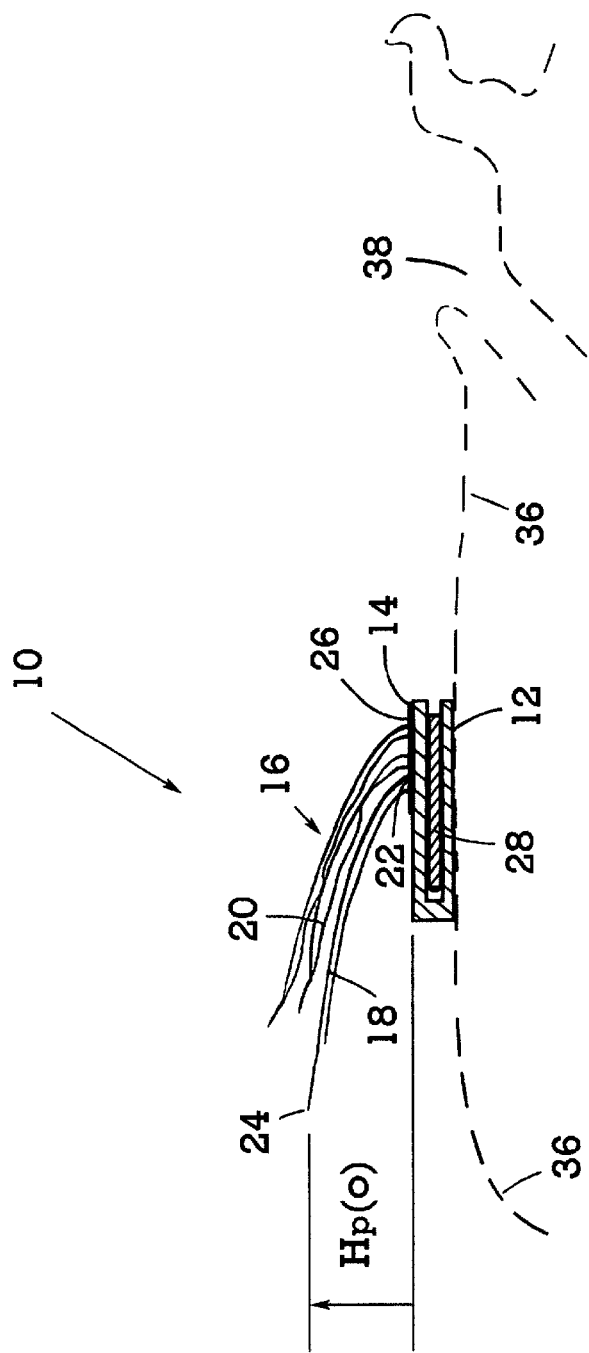
FIG. 1 is a sectional view of a forward tilted pile fastened to a base or helmet strap clip, including helmet strap and rider's cheekbone, temple and ear canal area.

Refer to FIG. 1. Helmet strap 28 of flexible aerodam 10 holds the base 12 snuggly against the temple or surface 36 of the rider's head. The flexible dam is located forward of the sound sensitive ear canal 38 so that the aeroacoustic effects caused by the dam are similar to the fixed aerodam, U.S. Pat. No. 6,029,769, with the improvement here that the dam is wind-reactive.

A commercially supplied acrylic fashion fur (AFF) 16 was used in the fabrication of the flexible aerodam 10 and was tested in bicycle helmet road tests. The variable height projection $H_p$ was created by using a style of AFF resembling mink with the tips of the fibers 24 mounted forward to point into a relative headwind $\bar{v}$, not shown in FIG. 1. The fibers are shown in the undisturbed position. A number of coarse, mechanically resilient matrix fibers 18 are endwise fastened at points 22 to a mat 14 by the supplier. Very thin flow resistant aeroacoustic fibers 20 are located amidst the coarse fibers 18 and are also attached to the mat. The mat 14 is then attached to base 12. The bottom third of each fiber lies about 20 to 30 degrees outward from the outer surface 26 of the mat 14 on which the AFF is manufactured. The fibers of type 18 and 20 then curve gradually to parallel the surface of the mat 14, each fiber tapering to a point giving a natural mink coat appearance in texture and color. The fibers 18 and 20 are mixed in thickness and location.

Figure 2:
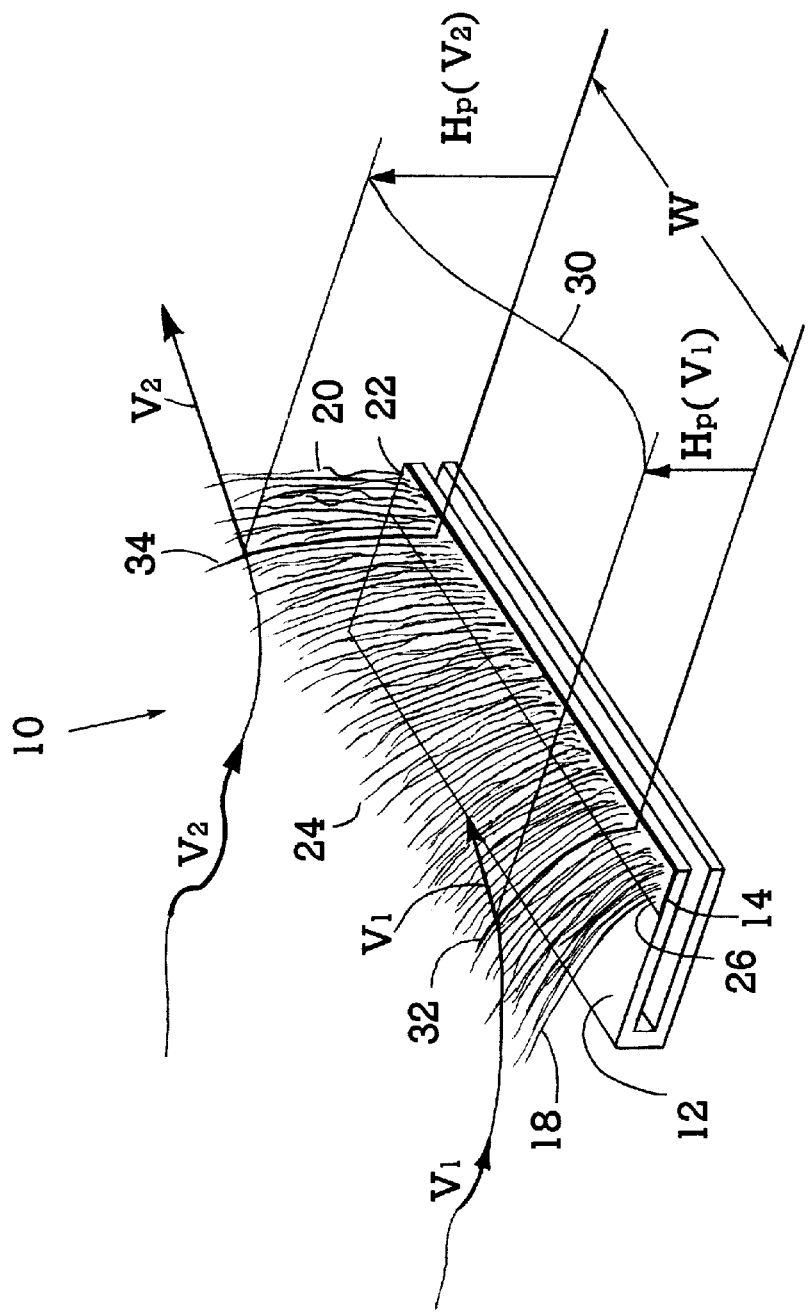
FIG. 2 shows the helmet strap clip base and the forward tilted fiber pile being blown upward to a projected height $H_p$ in response to headwind v. A height profile curve is included. Bicycle helmet strap and cheekbone area are not shown.

See FIG. 2. As the instantaneous wind v increases, the small, numerous fibers 20 resists the wind pressure and catch the air so that the fiber mass 16 begins to stand up at a higher camber angle; the rising action resisted only by the stiffness of the larger fibers 18. The result presents a higher projected height $H_p(v)$ than its zero wind, lay-down position. So $dH_p/dv=K>0$, where K is either a constant or a positive function of v. The multi-element structure of stiff fibers 18 flex independently across the width W of the dam. The higher the local wind velocity $v_2$ the higher the local $H_p(v_2)$, as shown by the darkened fiber 34; whereas as the velocity $v_1$ decreases, so does $H_p(v_1)$ commensurately decrease, as shown by the enhanced fiber 32. A profile of the reaction height $H_p$ across W is shown by curve 30. In general, the time dependent velocity gradient caused by the turbulence across the width W of the aerodam produces a proportional time dependent impedance gradient across the same dimension. Not only do the fine fibers act as flow impedance elements, but they also act as a filter for vortex damping and velocity profile control as previously described in U.S. Pat. No. 6,029,769.

The AFF is a hardy survivor of rough handling. It is also easily fabricated onto a base or for direct mounting onto a helmet strap, for instance. The AFF is manufactured by the supplier to include a foundation cloth or mat. So for the fabricator, by turning the AFF over to expose the underside of the cloth, the fabricator simply glues the outer surface of a base onto the exposed underside, then a cut is made in the cloth along the edge of the base. The resulting base with fur attached is then withdrawn from the cordage of the AFF and the assembly, as shown in FIG. 2 is complete except for the trim.

OPERATION

In headwind turbulence the Bernoulli pressure along the overflow, $p_o$, varies commensurately with the varying height of the dam, $H_p$. The pressure-to-height ratio $p_o/H_p$ must then be adjusted to keep the ear canal pressure $p_e$ constant so that locally heard turbulence is reduced or eliminated. To do this one must search for the proper value or function of K(v) to allow the ear canal pressure variation $dp_e/dt$ to approach zero.

The above argument is based on incoming vortex diameters D being much larger than W. When D is smaller than W the fibers of the acrylic fur act individually so as to compromise and average out the turbulent pressure changes across the width. That is why the fibers are chosen to move independently of one another.

In searching for the proper value of K and its function with v, various values of the restoring torque of the fiber pile 16 can be made by cutting or shaping the pile for zero pressure variation at the ear canal. In all this design effort, the ambient sounds are simply not affected so the signal-to-noise ratio is very high.

The length of the mat 14 which is parallel to the wind and is usually quite short, suggests that just a few support fibers 18 with attendant filter fibers 20 are all that are needed along the length or flow line dimension. If the fiber mass 16 rises as a homogeneous group then the longer the mat, and the more the fibers are constricted by friction, the less sensitive is K. Extra batting such as STTC 603 mentioned frequently in U.S. Pat. No. 6,029,769 can be inserted and lightly fastened to the mat or the AFF fibers to increase K and also to aid the fine impedance fibers 20 in damping local vortices. The added batting also alters the velocity profile of the flow envelope. If friction-free fibers on the upper portion of the fiber pile 16 have a smaller stiffness and the fibers rise heterogeneously instead of all at once, then the upper fiber mass will rise first. If the wind instantaneously increases, as turbulence tends to do, the additional lower matrix fibers will commensurately rise. This heterogeneous backup system can create a very broad range of values of K for a very wide spectrum of gust speeds v, so the dynamic reponse of the dam can be made broad in intensity as well as reaction time. Alternatively, the fibers in the rear of pile 16 can be cut shorter so that they buttress the longer frontal fibers. This broadens the speed range considerably but it compromises the look of the fur which may be important in styling.

Dynamic regulation of the envelope ceases when the matrix fibers reach an angle of 90° with respect to the base. So there is a wind speed limit as far as K is concerned. As mentioned above, the sensitivity K is lowered by increasing the length of the AFF patch. For low speed regulation, 20 to 30 miles per hour, an AFF patch length of 3/16 inch will do. For higher speeds the length should increase to 3/4 inch or more.

There are many types of lean-to fiber materials, composites, and designs that could be used for the above application. The AFF was chosen because it looks nice on the helmet strap.

APPLICABILITY AND ADVANTAGES

Suggested uses of flexible, anti parallel matrix flow stabilizers in a turbulent flow medium might also cover microphone and hydrophone protection along the side of a containing body. Other uses might encompass wake stabilization on control surfaces, or in lieu of control surfaces in certain cases.

The advantage over fixed covers or absorbers is the variable porosity gradient where the flow control enlists a negative feedback of flow impedance near the surface between the oncoming wind and the device being protected.

Other embodiments that incorporate the principles above may be constructed by anyone skilled in the art. In this respect it remains for an automated cellular routine using perhaps a modified Navier-Stokes differential vector program to solve the aeroelastic dynamics posed herin.

SUMMARY

In a headwind the flow velocity profile or envelope wake alongside the human ear should be as steady as possible for quiet flow. The porous aerodam in the prior art is used for this purpose. However, in a headwind with preturbulence the flow is anything but steady, vibrating the envelope creating infranoise which distracts from the desired ambient sounds.

A porous tilt-up dam which is flexibly reactive to wind pressures is placed at the temple area of the person's head so that the projected height $H_p$ of the dam changes commensurately with changes in local flow velocity v. Expressed differentially, $dH_p/dv$ is equal to a positive function. This ensures that the slope of the local velocity profile, or envelope, remains unchanged, thus the turbulent infranoise is reduced.

An acrylic artificial mink fur patch was used for the reactive porosity. A fur patch was mounted on each temple of a bicycle rider's head and oriented anti parallel to the local wind direction, the hairs rising higher as the headwind increased. The local velocity profile was stabilized and gust sounds were reduced.

A hearing aid worn behind or in the ear can also be protected from turbulent flow. Indeed, any sound sensitive device enclosed in a bluff body could be better protected from turbulent interference.

What is claimed is:

1. A wind noise reducing, boundary layer flow regulating dam to be worn on a band around a wearer's head so that the dam rests on the temple area, the wearer facing a turbulent headwind; the dam comprising a base having a width perpendicular to said wind, a length parallel to the wind, an inner surface defined by said length and width and having attachable means for attachment to said band, the base having an outer surface;

a matrix comprising said outer surface including an air flow permeable superstructure fastened to said outer surface and having a height normal to the outer surface, said superstructure being flexibly resistant in response to said turbulent headwind;

a fibrous aerodynamically porous maze supported and attached to at least part of said matrix to impede but not arrest air flow and to damp out vortices caused by the matrix structure;

the combination of the matrix and maze comprising an aerodynamically moved flexible filter having a thickness parallel to said length, said thickness tapering in permeability as a function of height from the outer surface;

whereby said filter causes a tortuous path flow impedance gradient to change in direct response to the turbulent variations of the headwind for a dynamically reduced infranoise pattern between the temple area and continuing past the wearer's ear canal.

2. The dam of claim 1 wherein at least a portion of said superstructure lies approximately parallel to the plane of the outer surface.

3. The dam of claim 1 wherein the superstructure is flexible at a joint connecting the superstructure with the outer surface of the base.

4. The dam of claim 1 wherein the superstructure is fibrous.

5. The dam of claim 1 wherein the superstructure comprises a monocoque structure.

6. The dam of claim 1 wherein the superstructure comprises a plurality of elements attached to the outer surface.

7. The dam of claim 6 wherein the elements are filaments with the free ends of each filament being outboard of the outer surface of the base.

8. The filaments of claim 7 wherein the filaments lean along the length direction and antiparallel to the direction of the headwind.

9. The dam of claim 1 wherein the inner surface of the base is fastened to a front helmet strap of a wearer's helmet.

10. The dam of claim 1 wherein the inner surface facilitates a resilient, non permeable means of attachment between the base and the wearer's head.

11. A method for filtering turbulent flow into a smoother wake along a pre-existing surface comprising passing said flow through a filtering maze held in position by a flexible resilient matrix; the combination of maze and matrix causes a moving flow porosity gradient commensurate with direction and velocity of the approaching turbulence along the surface.

12. A method of claim 11 wherein the matrix is formed as a single, flexible, monocoque structure.

13. A method of claim 11 wherein the matrix is formed with projections to create an aerodynamically, semi porous maze.

14. A method of claim 11 wherein the matrix is formed of independently flexible supporting elements.

15. An improved method of claim 14 wherein the matrix is formed of different sized elements.

16. An improved method of claim 15 wherein the matrix is formed from a selection of a pre-existing plurality of flow resistant, resiliently flexible elements.

17. A method of claim 11 whereby a base is formed having an inner part with fastening means for fastening to said pre-existing surface, and an outer part comprising a supporting structure.

18. A method of claim 17 wherein fabrication of said filter comprises:
   selecting a pre-existing artificial fur comprising thick filaments which act as a matrix, and thin filaments which act as a filter, all filaments laying somewhat parallel to each other at a predetermined approximate angle of repose with respect to a mat on which the filaments are attached, the mat having a bottom surface;
   cementing said bottom surface to said outer part of the base;
   trimming the mat to said dimensions of the base;
   whereby fastening the inner surface of the base to said pre-existing surface allows an incoming turbulent wind flowing anti parallel to said parallel direction of the filaments to cause the filaments to fluctuate in a direction normal to the base from said predetermined angle of repose to generate an instantaneous change in flow impedance to calm the wake from gust surges.

19. A boundary layer flow regulating dam comprising a base with attachment element for attachment to a pre-existing surface, the base having a width perpendicular to an incoming wind, the base including an outer part;
   a group of fine elements having an aerodynamic impedance to facilitate an aerodynamic force caused by said wind and supported by at least one shaped, flexibly resistant element attached to said outer part;
   whereby a wind passing said fine elements exert a torque on the supporting element or elements to change the shaped permeability density so that the fine elements reposition, causing an aerodynamic change in the wake commensurate with the instantaneous vector strength of the headwind.

20. A regulating dam as in claim 19 wherein said group of elements are flexibly attached to each other.

* * * * *